US010107738B2

(12) United States Patent
Tomida

(10) Patent No.: US 10,107,738 B2
(45) Date of Patent: Oct. 23, 2018

(54) MOISTURE STATUS MEASURING DEVICE THAT MEASURES MOISTURE STATUS IN SOIL, MOISTURE STATUS MEASURING METHOD, AND NON-TRANSITORY COMPUTER-READABLE MEDIUM STORING A PROGRAM

(71) Applicant: CASIO COMPUTER CO., LTD., Tokyo (JP)

(72) Inventor: Takahiro Tomida, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 319 days.

(21) Appl. No.: 13/973,806

(22) Filed: Aug. 22, 2013

(65) Prior Publication Data

US 2014/0060164 A1    Mar. 6, 2014

(30) Foreign Application Priority Data

Sep. 6, 2012 (JP) ................................. 2012-195722

(51) Int. Cl.
*G01N 5/02* (2006.01)
*G01N 19/10* (2006.01)
(Continued)

(52) U.S. Cl.
CPC ........... *G01N 19/10* (2013.01); *A01G 25/167* (2013.01); *G01N 33/26* (2013.01)

(58) Field of Classification Search
CPC ........ G01N 5/02; G01N 19/10; G01N 27/048; G01N 27/223
(Continued)

(56) References Cited

U.S. PATENT DOCUMENTS 4,937,972 A * 7/1990 Freitus ................. A01G 27/003
47/62 R
2008/0190020 A1* 8/2008 Todd .................... A01G 27/001
47/48.5
(Continued)

FOREIGN PATENT DOCUMENTS

CN          102150577 A    8/2011
JP          03137551 A     6/1991
(Continued)

OTHER PUBLICATIONS

Chinese Office Action dated Dec. 29, 2014, issued in counterpart Chinese Application No. 201310397185.X.
(Continued)

*Primary Examiner* — John Fitzgerald
*Assistant Examiner* — Rodney T Frank
(74) *Attorney, Agent, or Firm* — Holtz, Holtz & Volek PC

(57) ABSTRACT

A moisture status measuring device includes a moisture amount sensor that acquires an output value according to an amount of moisture contained in soil, a drainage sensor that detects water discharge from the soil, and a moisture status deriver that derives moisture status information expressing a moisture status of the soil based on the output value acquired by the moisture amount sensor and detection of the water discharge by the drainage sensor. Every time when the drainage sensor detects the water discharge, the moisture status deriver acquires the output value at a time when the drainage sensor detects the water discharge. The moisture status deriver derives moisture status information expressing the moisture status of the soil at an arbitrary time based on the output value acquired at the time when the drainage sensor detects the water discharge and the output value at the arbitrary time.

20 Claims, 6 Drawing Sheets

(51) Int. Cl.
*A01G 25/16* (2006.01)
*G01N 33/26* (2006.01)

(58) Field of Classification Search
USPC .............................................................. 73/73
See application file for complete search history.

(56) References Cited

U.S. PATENT DOCUMENTS

| | | | |
|---|---|---|---|
| 2008/0199359 A1 | 8/2008 | Davis et al. | |
| 2009/0025287 A1* | 1/2009 | Lee | A01G 7/00 47/17 |
| 2009/0293354 A1* | 12/2009 | Goldberg | A01G 25/167 47/66.6 |
| 2010/0253369 A1 | 10/2010 | Izadnegahdar | |
| 2011/0154985 A1* | 6/2011 | Mittelmark | A01G 27/00 95/1 |
| 2012/0297675 A1 | 11/2012 | Hashimoto et al. | |

FOREIGN PATENT DOCUMENTS

| | | | |
|---|---|---|---|
| JP | 08271459 | A | 10/1996 |
| JP | 2608679 | B2 | 5/1997 |
| JP | 01141531 | A | 2/1999 |
| JP | 11243796 | A | 9/1999 |
| JP | 2001251978 | A | 9/2001 |
| JP | 2005265664 | A | 9/2005 |
| JP | 2012132794 | A | 7/2012 |

OTHER PUBLICATIONS

Japanese Office Action (and English translation thereof) dated Feb. 2, 2016, issued in counterpart Japanese Application No. 2012-195722.

Japanese Office Action (and English translation thereof) dated Apr. 5, 2016, issued in counterpart Japanese Application No. 2012-195722.

Japanese Office Action dated Dec. 19, 2017 issued in Japanese Application No. 2017-003751.

* cited by examiner

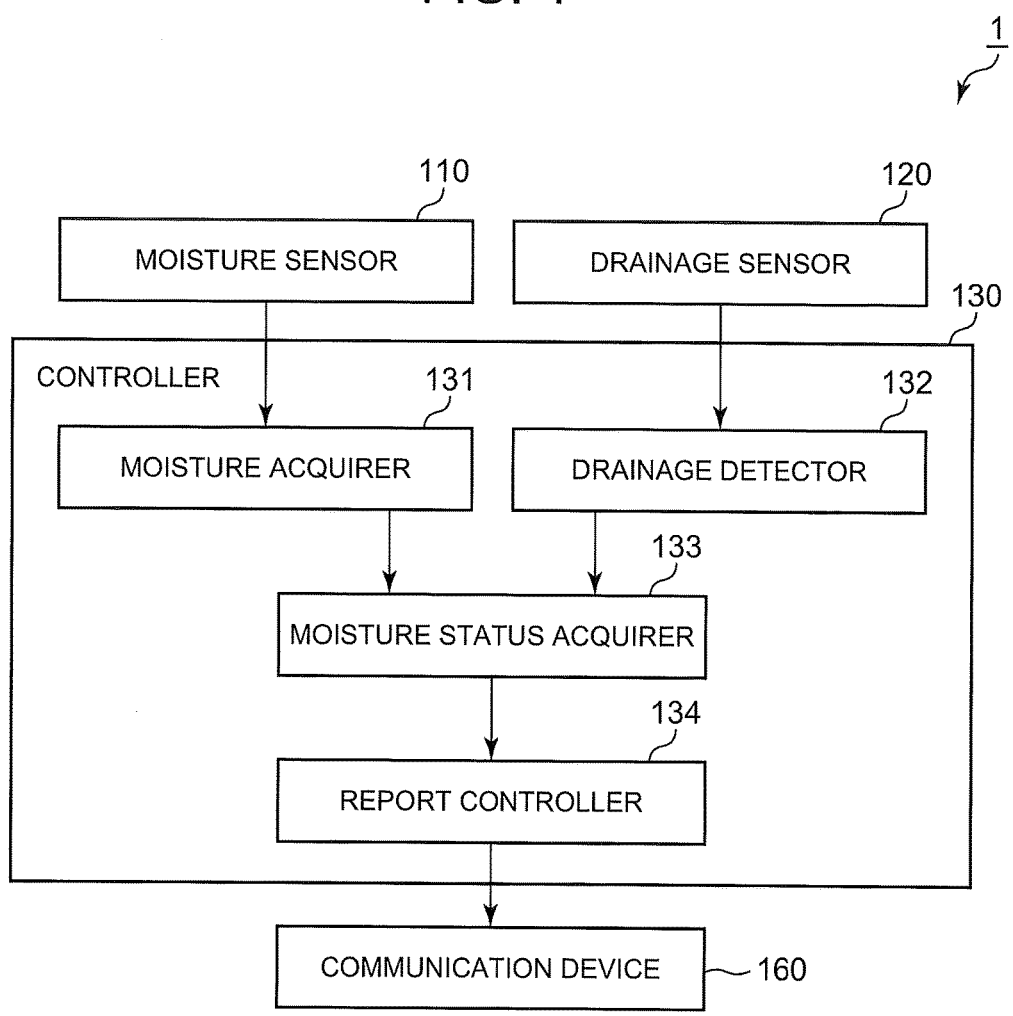

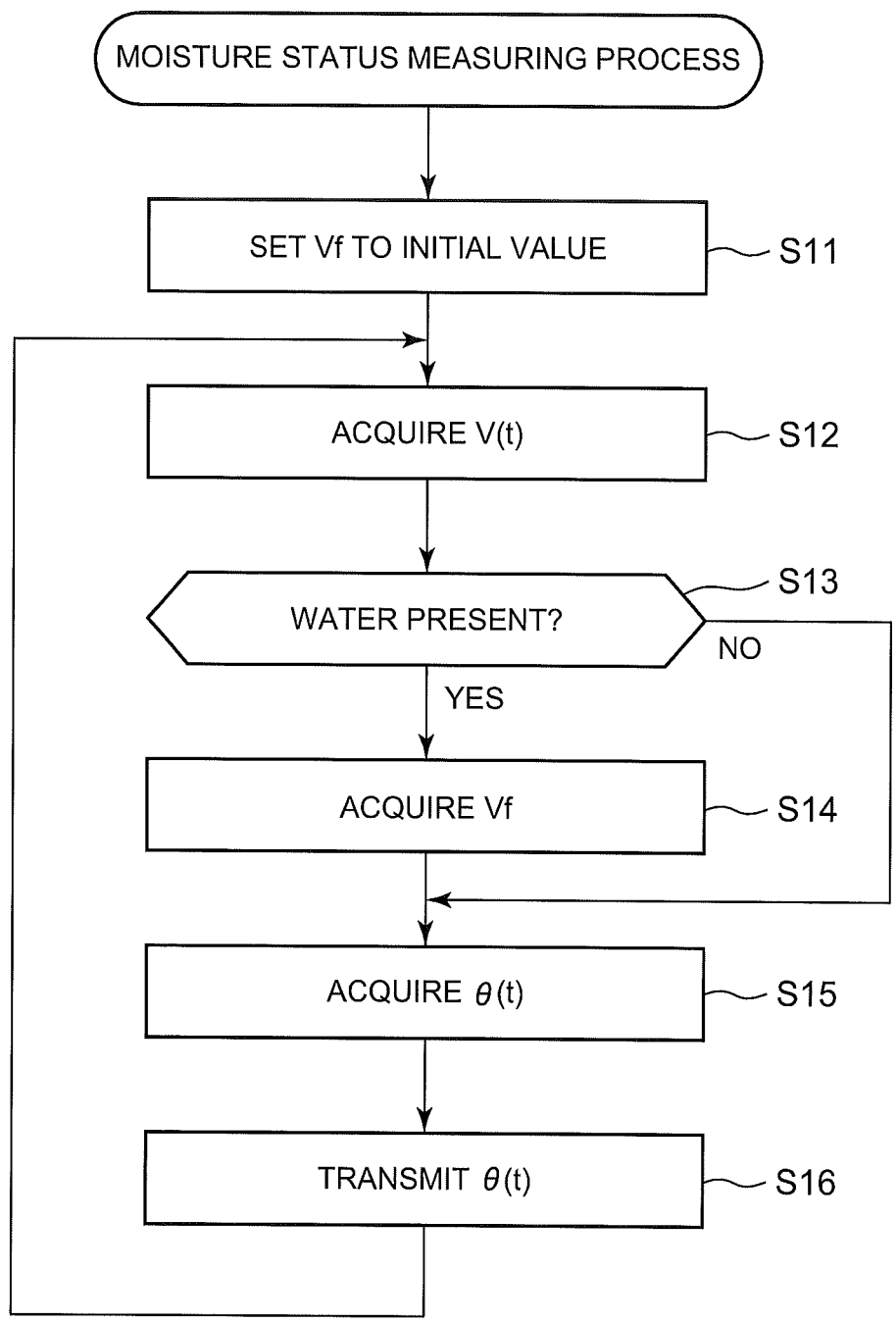

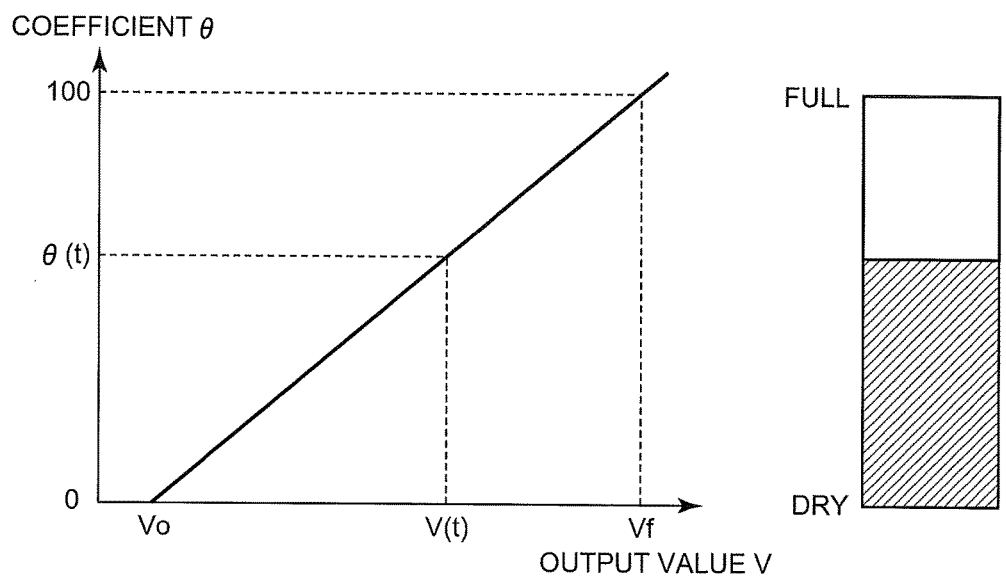
FIG. 6A
FIG. 6B
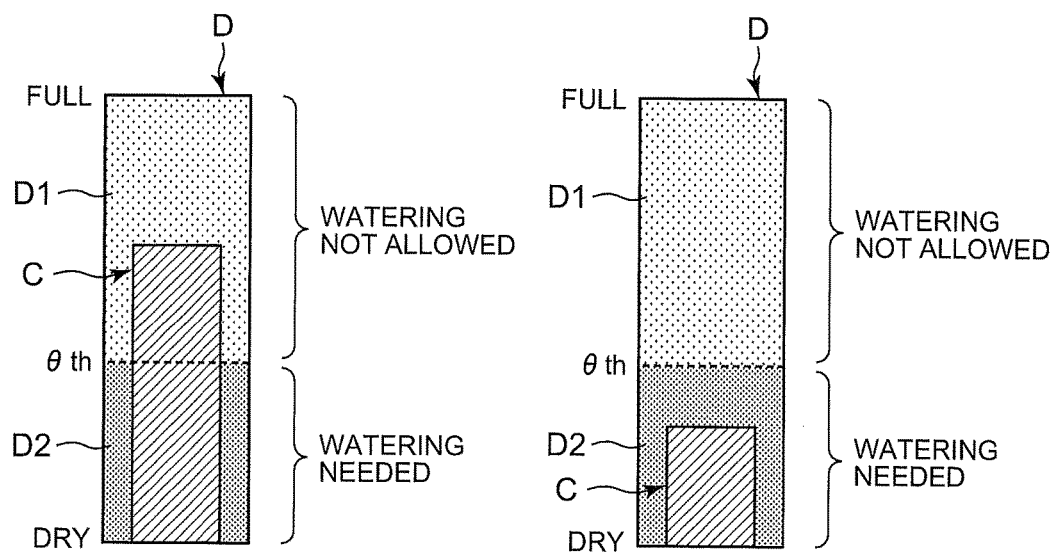
FIG. 7A
FIG. 7B

FIG. 8

TYPE-SPECIFIC THRESHOLD VALUE TABLE

| PLANT TYPE | TYPE-SPECIFIC THRESHOLD VALUE |
|---|---|
| MONSTERA | $\theta$ th-m |
| PACHIRA | $\theta$ th-p |
| POTHOS | $\theta$ th-e |
| SANSEVIERIA | $\theta$ th-s |
| CACTUS | $\theta$ th-c |
| ⋮ | ⋮ |

MOISTURE STATUS MEASURING DEVICE THAT MEASURES MOISTURE STATUS IN SOIL, MOISTURE STATUS MEASURING METHOD, AND NON-TRANSITORY COMPUTER-READABLE MEDIUM STORING A PROGRAM

CROSS-REFERENCE TO RELATED APPLICATION

This application claims the benefit of Japanese Patent Application No. 2012-195722, filed on Sep. 6, 2012, the entire disclosure of which is incorporated by reference herein.

FIELD

This application relates to a moisture status measuring device that measures the status of moisture in soil, to a moisture status measuring method, and to a non-transitory computer-readable medium that stores a program.

BACKGROUND

Among methods of measuring the amount of moisture in soil, there exists an Amplitude Domain Reflectometry (ADR) method and a Time Domain Reflectometry (TDR) method, for example. These methods utilize the property that electric permittivity increase as the amount of moisture in soil increases. By electrically measuring the permittivity, the amount of moisture in soil is measured. Also, as a method of measuring the amount of moisture in soil, there exists a moisture content monitoring device that includes multiple electrodes able to be inserted into gardening soil. By measuring the electrical resistance value between these electrodes, the moisture content monitoring device measures the moisture content, and emits a warning sound in the case where the moisture content becomes less than or equal to a set boundary level (see Japanese Patent No. 2608679, for example).

SUMMARY

However, with a method that measures moisture content from electrical permittivity such as that described in Japanese Patent No. 2608679, the electrical permittivity differs if the soil itself differs, even if the soils were to hypothetically have the same moisture content by volume. For this reason, differing measurement results are obtained. Consequently, since the amount of moisture of some soils cannot be accurately measured, sufficiently managing the moisture status in that soil is difficult.

The present invention has been devised in light of such problems, and takes as an objective to provide a moisture status measuring device, moisture status measuring method and a non-transitory computer-readable medium that stores a program enabling measurement of the moisture status of moisture in soil housed in a container.

In order to achieve the above objective, a moisture status measuring device according to the present invention is provided with:

a moisture amount sensor that acquires an output value according to an amount of moisture contained in soil;

a drainage sensor that detects water discharge from the soil; and a moisture status deriver that derives moisture status information expressing a moisture status of the soil based on the output value acquired by the moisture amount sensor and the detection of the water discharge by the drainage sensor;

wherein the moisture status deriver derives the moisture status information according to the following formula:

$$\theta(t) = \frac{V(t) - V_o}{V_f - V_o} \times 100$$

where:

$\theta(t)$ is the moisture status information, $V(t)$ is a voltage value acquired by the moisture amount sensor as the output value at an arbitrary time t, $V_f$ is a voltage value acquired by the moisture amount sensor as the output value at a time when the drainage sensor detects the water discharge, and $V_o$ is a voltage value acquired by the moisture amount sensor as the output value in a state of dry soil.

A moisture status measurement method according to the present invention includes:

acquiring an output value according to an amount of moisture contained in soil;

detecting water discharge from the soil; and deriving moisture status information expressing a moisture status of the soil based on the acquired output value and the detection of the water discharge;

wherein the moisture status information is derived according to the following formula:

$$\theta(t) = \frac{V(t) - V_o}{V_f - V_o} \times 100$$

where:

$\theta(t)$ is the moisture status information, $V(t)$ is a voltage value acquired as the output value at an arbitrary time t, $V_f$ is a voltage value acquired as the output value at a time when the water discharge is detected, and $V_o$ is a voltage value acquired as the output value in a state of dry soil.

A non-transitory computer-readable medium according to the present invention stores a program, the program being executable by a computer of a moisture status measurement device including a moisture amount sensor and a drainage sensor, to control the moisture status measurement device to perform functions including:

acquiring an output value according to an amount of moisture contained in soil, by the moisture amount sensor;

detecting water discharge from the soil, by the drainage sensor; and deriving moisture status information expressing a moisture status of the soil based on the acquired output value and the detection of the water discharge;

wherein the moisture status information is derived according to the following formula:

$$\theta(t) = \frac{V(t) - V_o}{V_f - V_o} \times 100$$

where:

$\theta(t)$ is the moisture status information, $V(t)$ is a voltage value acquired by the moisture amount sensor as the output value at an arbitrary time t, $V_f$ is a voltage value acquired by the moisture amount sensor as the output value at a time when the drainage sensor detects the water discharge, and $V_o$ is a voltage value acquired by the moisture amount sensor as the output value in a state of dry soil.

According to the present invention, providing a moisture status measuring device that can measure the status of moisture in soil housed in a container, a moisture status measuring method, and a non-transitory computer-readable medium that stores a program is possible.

BRIEF DESCRIPTION OF THE DRAWINGS

A more complete understanding of this application can be obtained when the following detailed description is considered in conjunction with the following drawings, in which:

FIG. 4 is a block diagram illustrating a functional configuration of a controller in a moisture status measuring device according to an embodiment;

FIG. 5 is a flowchart illustrating an exemplary flow of a moisture status measuring process executed by a controller in a moisture status measuring device according to an embodiment;

FIG. 6A is a diagram illustrating the relationship between a voltage value output from a moisture sensor, and a moisture status coefficient;

FIG. 6B is a diagram illustrating an example of moisture status information displayed on a display of a communication terminal device;

FIG. 7A is a diagram illustrating an example of moisture status information displayed on a display of a communication terminal device;

FIG. 7B is a diagram illustrating an example of moisture status information displayed on a display of a communication terminal device; and FIG. 8 is a diagram illustrating an example of a type-specific threshold value table.

DETAILED DESCRIPTION

Hereinafter, an embodiment of the present invention will be described with reference to the drawings.

Figure 1:
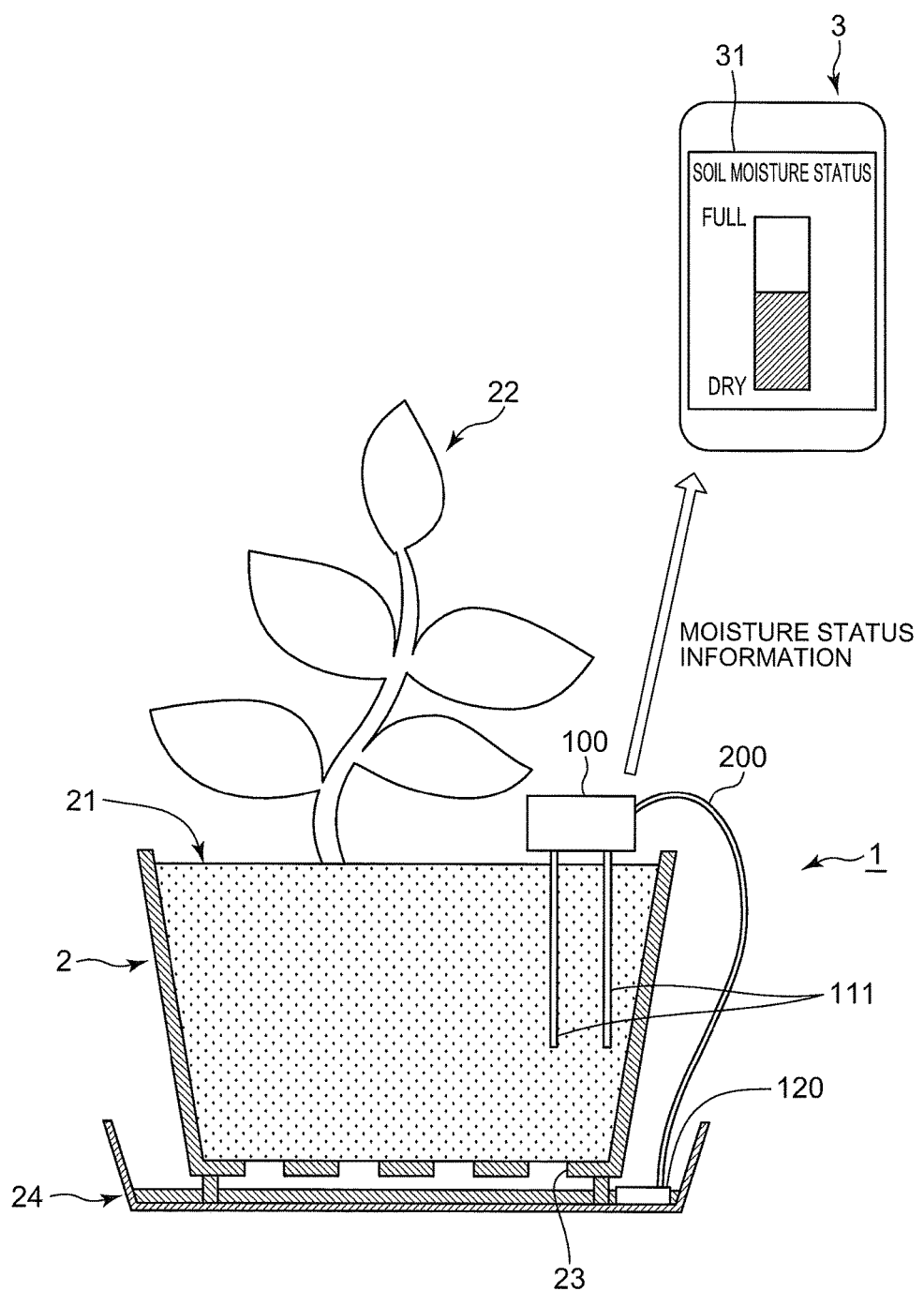
FIG. 1 is a diagram illustrating a moisture status measuring device according to an embodiment.

FIG. 1 is a diagrams illustrating exemplary usage of a moisture status measuring device 1 according to the present embodiment.

In the usage examples illustrated in FIG. 1, the moisture status measuring device 1 measures the moisture status of soil 21 housed in a pot 2. The moisture status measuring device 1 then transmits information expressing the measured moisture status (moisture status information) to a communication terminal device 3. Then communication terminal device 3 displays an image expressing the received moisture status information on a display 31.

The moisture status measuring device 1 is equipped with a main body 100, and a drainage sensor 120 communicably connected to the main body 100 by a wire 200. The main body 100 acquires moisture status information on the basis of output values from a moisture sensor 110 (see FIG. 2) that includes electrodes 111 inserted into the soil 21, and the drainage sensor 120, and transmits the acquired moisture status information to the communication terminal device 3. Note that a detailed configuration and operation of the moisture status measuring device 1 will be described later.

The pot 2 is a container housing the soil 21 in which a plant 22 is growing. Specifically, the pot 2 is configured in a shape having sidewalls and a bottom, with an open top. Also, the bottom of the pot 2 includes multiple drainage holes 23. Water poured in from above the soil 21 filters through the soil 21, and is discharged out from the drainage holes 23.

In addition, a saucer 24 is provided under the pot 2. The saucer 24 is able to collect water discharged from the drainage holes 23 of the pot 2 within a range that does not exceed the height of its sidewalls.

The communication terminal device 3 is a terminal device able to communicate with the moisture status measuring device 1, and is made up of a terminal device such as a mobile phone, for example. The communication terminal device 3 is equipped with a display 31, and displays moisture status information received from the moisture status measuring device 1. The communication terminal device 3 is also equipped with an input device (not illustrated) such as a touch panel, buttons, or keys, which receives input from the user, and transmits received information to the moisture status measuring device 1.

Next, a hardware configuration of a moisture status measuring device 1 according to the present embodiment will be described.

Figure 2:
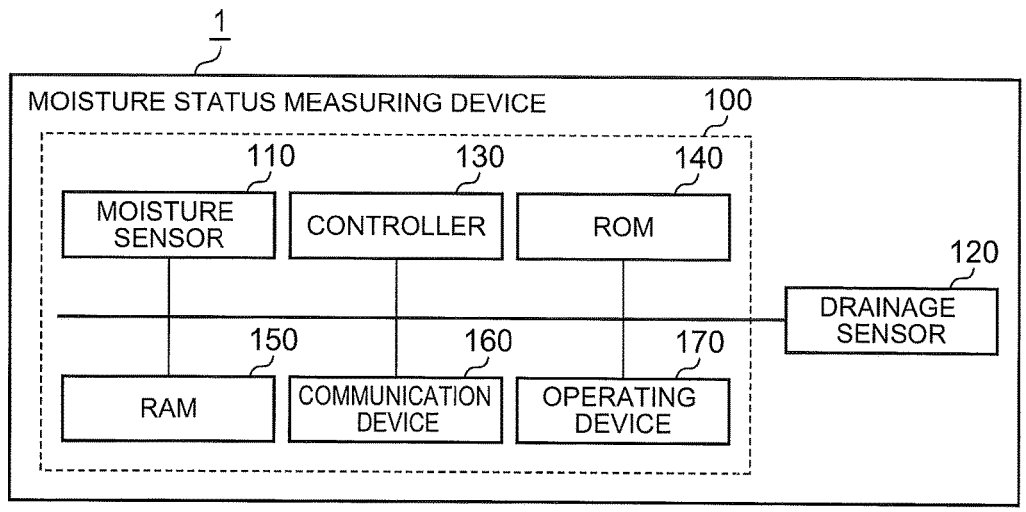
FIG. 2 is a schematic block diagram illustrating an exemplary hardware configuration of a moisture status measuring device according to an embodiment.

FIG. 2 is a block diagram that schematically illustrates an exemplary hardware configuration of a moisture status measuring device 1 according to the present embodiment. As illustrated in FIG. 2, the moisture status measuring device 1 is equipped with a moisture sensor 110, a drainage sensor 120, a controller 130, read-only memory (ROM) 140, random access memory (RAM) 150, a communication device 160, and an operating device 170. In addition, the moisture sensor 110, controller 130, ROM 140, RAM 150, communication device 160, and operating device 170 constitute the main body 100.

The moisture sensor 110 is a sensor that outputs an output value according to the amount of moisture contained in the soil 21. A typical moisture sensor using the ADR method, for example, is potentially used as the moisture sensor 110. The moisture sensor 110 includes electrodes 111 (see FIG. 1) inserted into the soil 21. The moisture sensor 110 then detects a voltage value according to the moisture in the soil 21 as an output value, which is input into the controller 130.

Figure 3:
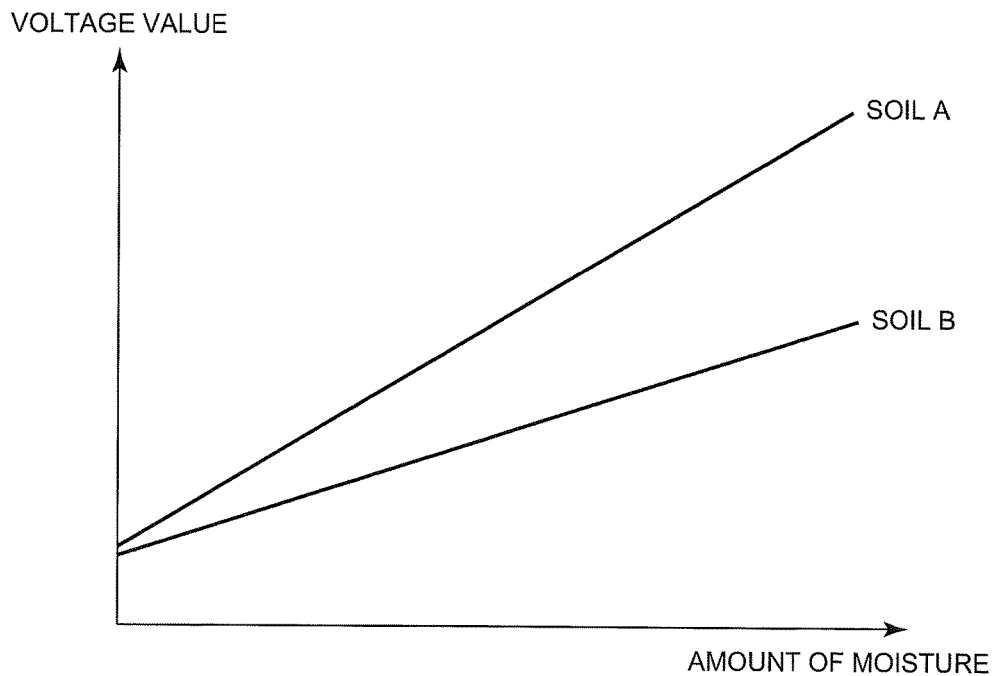
FIG. 3 is a diagram illustrating the relationship between a voltage value output by a moisture sensor, and the amount of moisture per unit volume contained in soil.

The relationship between the voltage value output by the moisture sensor 110 and the amount of moisture contained in soil will now be described. FIG. 3 is a diagram illustrating the relationship between the voltage value output by the moisture sensor 110, and the amount of moisture per unit volume contained in soil. Note that FIG. 3 illustrates the relationship between the voltage value and the amount of moisture for two soils A and B with different components constituting the soil. As illustrated in FIG. 3, for both soils A and B, the detected voltage value linearly increases as the amount of moisture increases. In this way, a moisture sensor 110 according to the present embodiment outputs voltage values in a linear relationship with the amount of moisture contained in soil.

The drainage sensor 120 is a sensor that detects water discharged from the drainage holes 23. The drainage sensor 120 is made up of a typical leak sensor, for example. The drainage sensor 120 is provided in the saucer 24, and detects water discharged from the drainage holes 23 by detecting the water collected in the saucer 24. Specifically, the drainage sensor 120 includes electrodes (not illustrated), and outputs the voltage value between the electrodes to the controller 130. The controller 130 detects the water in the saucer 24 on the basis of the output value from the drainage sensor 120. Note that the drainage sensor 120 is not limited to a leak sensor. An arbitrary sensor is applicable insofar as the sensor is able to detect water in the saucer 24.

The controller 130 is made up of a central processing unit (CPU), for example, and controls the moisture status measuring device 1 overall.

The ROM 140 is non-volatile memory that stores programs and data by which the controller 130 controls the moisture status measuring device 1 overall. For example, the ROM 140 stores a program by which the controller 130 executes a moisture status measuring process discussed later.

The RAM 150 is made up of non-volatile memory such as flash memory. The controller 130 loads a program being stored in the ROM 140 into the RAM 150, which is used as a work area.

The communication device 160 is made up of a wireless communication device or the like, for example, it connects to a given network as necessary, and communicates with the communication terminal device 3.

The operating device 170 is made up of input devices such as buttons for operating the moisture status measuring device 1. The operating device 170 receives from the user an input operation indicating to start measurement of the moisture status, which is input into the controller 130.

Next, a functional configuration of the controller 130 of the moisture status measuring device 1 will be described. FIG. 4 is a block diagram illustrating a functional configuration of the controller 130 in a moisture status measuring device 1 according to the present embodiment. As illustrated in FIG. 4, the controller 130 functions as a moisture acquirer 131, a drainage detector 132, a moisture status acquirer 133, and a report controller 134.

The moisture acquirer 131 acquires, from the moisture sensor 110, an output value according to the amount of moisture contained in the soil 21. Specifically, the moisture acquirer 131 acquires a voltage value detected by the moisture sensor 110 at a given time interval.

The drainage detector 132 detects water discharged from the drainage holes 23 on the basis of an output value from the drainage sensor 120. Specifically, the drainage detector 132 acquires a voltage value detected by the drainage sensor 120 at a given time interval. The drainage detector 132 then determines whether or not water has been detected on the basis of the acquired voltage value.

The moisture status acquirer 133 acquires moisture status information expressing the current moisture status of moisture in the soil 21, on the basis of the output value from the moisture sensor 110 at the time when the drainage sensor 120 detected water, and the current output value from the moisture sensor 110.

Herein, in the present embodiment, the moisture status acquirer 133 acquires, as the moisture status information, a moisture status coefficient θ indicated as a degree of moisture, taking 0 to be a state in which the soil 21 is dry, and 100 to be the state of the soil 21 at the time when water is discharged from the drainage holes 23.

Next, an example of an acquisition method for the moisture status coefficient θ by the moisture status acquirer 133 will be specifically described. Provided that V(t) is the voltage value acquired by the moisture acquirer 131 at a time t, Vf is the voltage value acquired by the moisture acquirer 131 at the time when the drainage detector 132 detected water, and Vo is the voltage value output by the moisture sensor 110 in a state of dry soil, the moisture status coefficient θ(t) at time t is expressed by the following Eq. 1.

$$\theta(t) = \frac{V(t) - V_o}{V_f - V_o} \times 100 \qquad (1)$$

Herein, Vo is a voltage value measured by the moisture sensor 110 for the soil 21 or another soil, for example, in a state in which that soil is dry, and is stored in the ROM 140 in advance. Note that the relative permittivity of soil in a completely dry state is conceivably small, with little fluctuation due to factors such as the soil properties. Consequently, a voltage value measured by the moisture sensor 110 in standard soil in a dry state that is preset as Vo is still usable in the computation of the moisture status coefficient θ in the present embodiment, since the difference in the computed moisture status coefficient θ is not large compared to the case of setting a voltage value measured by the moisture sensor 110 in the soil 21 in a dry state as Vo.

The report controller 134 transmits moisture status information acquired by the moisture status acquirer 133 to the communication terminal device 3 (see FIG. 1) via the communication device 160. Transmitted moisture status information is displayed on the display 31.

Next, operation of a moisture status measuring device 1 according to the present embodiment will be described with reference to the drawings. FIG. 5 is a flowchart illustrating an exemplary flow of a moisture status measuring process executed by the controller 130 in a moisture status measuring device 1 according to the present embodiment. Note that this moisture status measuring process is assumed to be stored in advance as a program in the ROM 140 discussed earlier, with the actual process being conducted due to the controller 130 reading out and executing the program.

The controller 130 of the moisture status measuring device 1 starts the moisture status measuring process illustrated in FIG. 5 when triggered by the user operating the operating device 170, for example.

First, the moisture status acquirer 133 substitutes an initial value into Vf (step S11). Note that the initial value to substitute is assumed to be stored in advance in the ROM 140, for example.

Next, the moisture acquirer 131 acquires a voltage value V(t) at a given time interval from the moisture sensor 110 (step S12). The moisture acquirer 131 then stores the acquired voltage value V(t) in the RAM 150, for example.

Next, the drainage detector 132 determines whether or not water discharged from the drainage holes 23 has been detected, on the basis of a voltage value acquired from the drainage sensor 120 (step S13). In the case of determining that water has not been detected (step S13; No), the drainage detector 132 proceeds to step S15.

In the case of determining that water has been detected (step S13; Yes), the moisture status acquirer 133 acquires, as Vf, the V(t) acquired at the time when water was detected (step S14). Specifically, from the RAM 150 the moisture status acquirer 133 acquires, as Vf, the most recent voltage value V(t) acquired by the moisture acquirer 131 at the time when the drainage detector 132 determined that water was present.

Next, the moisture status acquirer 133 uses Eq. 1 to acquire the current moisture status coefficient θ(t) from the most recent voltage value V(t) acquired by the moisture acquirer 131, Vf, and Vo at the current time (step S15).

Next, the report controller 134 transmits the moisture status coefficient θ(t) acquired in step S15 to the communication terminal device 3 via the communication device 160 (step S16). The process then returns to step S12.

The controller 130 repeatedly executes the processing in the above steps S12 to S16. In addition, the controller 130 ends the moisture status measuring process in the case of receiving input indicating to end the moisture status measuring process from the user via the operating device 170, for example.

The moisture status information displayed on the communication terminal device 3 will now be described. FIG. 6A is a diagram illustrating the relationship between the voltage value V output from the moisture sensor 110 and the moisture status coefficient θ, while FIG. 6B is a diagram illustrating an example of moisture status information displayed on the display 31 of the communication terminal device 3.

As illustrated in FIG. 6A, the moisture status coefficient θ is a value that varies linearly with respect to the voltage value V. The moisture status coefficient θ is 0 when the voltage value V is Vo, and the moisture status coefficient θ is 100 when the voltage value V is the voltage value Vf. The moisture status coefficient θ is expressed as a bar graph, an example of which is illustrated in FIG. 6B. Namely, in the case where the moisture status coefficient θ(t) is the acquired coefficient θ for a voltage value V(t) at time t, moisture status coefficient θ is expressed as a bar (the shaded portion in FIG. 6B) of height corresponding to the magnitude of that moisture status coefficient θ(t). With such a display, the user is easily able to ascertain the current moisture status of the soil 21. However, the display format of moisture status information is not limited thereto, and displaying the numerical value of the moisture status coefficient θ is also possible, for example.

According to a moisture status measuring device 1 configured as above, a moisture status coefficient θ is acquired as moisture status information, moisture status coefficient θ being a ratio of the current output value from a moisture sensor versus the output value from the moisture sensor 110 at the time when the drainage sensor 120 detected water from the drainage holes 23. Consequently, measuring the moisture status of moisture in arbitrary soil is possible.

In other words, the basic watering method of "generously provide water if the soil is dry" is a watering method that typically applies to almost all foliage plants. Herein, "generously" refers to an extent to which water drips out from the bottom of the pot, because providing water to this extent enables fresh air to enter into the soil. In the present embodiment, moisture status information is acquired whereby the moisture status is taken to be a "full" state for the amount of water at the time when water drips out from the pot 2 in which the plant 22 to be watered is planted. Consequently, measuring the moisture status is possible regardless of the type of soil.

Meanwhile, soil properties typically change over time. In the present embodiment, Vf is updated with every watering (see step S14 in FIG. 5), thereby enabling the acquisition of moisture status information that reflects the properties of the soil 21 at the time of measurement.

(Modification 1)

In the moisture status measuring device 1 according to the above embodiment, the report controller 134 reports moisture status information to the user by transmitting moisture status information acquired by the moisture status acquirer 133 to the communication terminal device 3, which is then displayed on the display 31. However, the device that reports moisture status information is not limited to the display 31, and an arbitrary reporting device is applicable.

For example, equipping the moisture status measuring device 1 with a display such as a liquid crystal display as a device that reports moisture status information is also possible. In this case, the report controller 134 is able to report moisture status information by displaying moisture status information on the display provided in the moisture status measuring device 1.

As another example, equipping the moisture status measuring device 1 with an audio output device such as a speaker or buzzer as a device that reports moisture status information is also possible. In this case, the report controller 134 is able to report moisture status information by controlling the audio output device to output moisture status information as audio.

As another example, equipping the moisture status measuring device 1 with a light emitter such as a light-emitting diode (LED) as a device that reports moisture status information is also possible. In this case, the report controller 134 is able to report moisture status information by turning the light emitter on/off and controlling the emitted color, emitted light intensity, and the like according to the moisture status information.

Also, not equipping the moisture status measuring device 1 itself with a reporting device such as the above audio output device and light emitter is also possible. For example, the report controller 134 transmitting moisture status information to a communication client device 3 equipped with an audio output device or light emitter is also possible. In this case, reporting moisture status information is possible with the audio output device or light emitter of the communication terminal device 3.

(Modification 2)

Additionally, in the above embodiment and Modification 1, the report controller 134 reports moisture status information acquired by the moisture status acquirer 133. However, the content and timing of the reporting by the report controller 134 is not limited thereto. For example, when the drainage sensor 120 detects drainage, the report controller 134 controls a reporting device provided in the moisture status measuring device 1 or the communication terminal device 3 to report that the moisture status of the soil 21 is full. In this way, when the drainage sensor 120 detects the discharge of water, it is possible to report to the user who waters the plant 22 that the moisture status of the soil 21 is full, thereby preventing overwatering.

(Modification 3)

Also, it is possible for the report controller 134 to report that watering the soil 21 is not allowed in the case where the moisture status expressed by moisture status information acquired by the moisture status acquirer 133 is a state of greater moisture than a moisture state of moisture in soil at a timing when watering the soil 21 is appropriate (hereinafter designated the "appropriate moisture status"). It is also possible for the report controller 134 to report that the soil 21 should be watered in the case where the moisture status expressed by moisture status information acquired by the moisture status acquirer 133 is a state of less moisture than the appropriate moisture status.

Specifically, the moisture status measuring device 1 stores a threshold value θth expressing the appropriate moisture status in advance in the ROM 140, for example. The report controller 134 then reports that watering the soil 21 is not allowed in the case where the moisture status coefficient θ acquired by the moisture status acquirer 133 is equal to or greater than the threshold value θth. Meanwhile, the report controller 134 reports that the soil 21 should be watered in the case where the moisture status coefficient θ acquired by the moisture status acquirer 133 is less than the threshold value θth.

FIGS. 7A and 7B illustrate moisture status information displayed on the display 31 as specific examples of a reporting format. The moisture status information illustrated in FIGS. 7A and 7B is expressed as a bar graph C having a height corresponding to the magnitude of the moisture status coefficient θ. In addition, the area D where the bar graph C is displayed is split into a partial area D1 corresponding to θth≤θ≤100 and a partial area D2 corresponding to 0≤θ≤θth, taking the position of a height corresponding to the magnitude of the threshold value θth as a boundary. Consequently, when the tip of the bar graph C is positioned inside the partial area D1 as illustrated in FIG. 7A, for example, the display 31 indicates that watering the soil 21 is not allowed. Meanwhile, when the tip of the bar graph C is positioned inside the partial area D2 as illustrated in FIG. 7B, for example, the display 31 indicates that the soil 21 should be watered. With such a display, the user is easily able to determine the timing for watering the soil 21.

As discussed above, the reason for providing water "if the soil is dry" is because even if water is generously provided, if the inside of the pot is in a continually wet state, the roots will be unable to breathe and thus rot, and the plant will wither. However, determining whether or not soil is in a dry state is difficult for beginners unaccustomed to growing plants. With respect to such a problem, in the moisture status measuring device 1 according to the present modification, a threshold value θth indicating an appropriate moisture state is preset, and a report indicating that watering is not allowed or that watering should be performed is issued on the basis of the threshold value θth and the current moisture status coefficient θ. For this reason, the user is easily able to determine whether or not the soil 21 is dry, or in other words, whether or not the timing is appropriate for watering.

(Modification 4)

In the above Modification 3, it is also possible for the moisture status measuring device 1 to store, in the ROM 140, type-specific threshold values expressing the appropriate moisture states for growing particular types of plants, for example.

FIG. 8 illustrates an example of a type-specific threshold value table stored in the ROM 140. The plant type-specific threshold value table illustrated in FIG. 8 stores, for individual types of plants, a type-specific threshold value expressing the appropriate moisture status of soil in which that type of plant will grow. For example, in the case where the type of plant is "Monstera", a type-specific threshold value "θth-m" expressing the appropriate moisture status of soil in which "Monstera" will grow is stored in association with "Monstera".

In this case, the user selects, from the type-specific threshold value table, the type of plant corresponding to the plant 22 growing in the soil 21. The report controller 134 then specifies the type-specific threshold value corresponding to the selected type of plant from the type-specific threshold value table. The report controller 134 then treats the specified type-specific threshold value as the threshold value θth, and reports that watering is not allowed or that watering should be performed, similarly to Modification 3. Thus, it is possible to report that watering is not allowed or that watering should be performed at timings appropriate to the plant 22 actually growing in the soil 21.

The foregoing thus describes an embodiment of the present invention and modifications thereof. However, the present invention is not limited to the above embodiment and modifications thereof.

For example, a drainage sensor 120 is provided in the saucer 24, and detects water discharged from the drainage holes 23 by detecting the water collected in the saucer 24. However, the position where the drainage sensor 120 is provided is not limited to the above. For example, in the case where a saucer 24 is not provided under the pot 2, the drainage sensor 120 may be provided on the edge of a drainage hole 23. The position where the drainage sensor 120 is provided is arbitrary insofar as the detection of water discharged from the drainage holes 23 is possible.

Also, although the above embodiment and modifications describe an example of acquiring a moisture status coefficient θ as moisture status information expressing the moisture status of the soil 21, the format of expressing the moisture status is not limited thereto. The current moisture status of the soil 21 is expressible in an arbitrary format, insofar as the format is expressed as a comparison between an output value from a moisture sensor at the time when the drainage sensor 120 detected water, and the current output value from the moisture sensor.

Also, although Vf is taken to be a voltage value acquired by the moisture acquirer 131 at a time when the drainage detector 132 detected water, it is also possible to take Vf to be a voltage value acquired by the moisture acquirer 131 several seconds after the drainage detector 132 detected water.

In addition, the moisture status measuring device 1 according to the present invention is realizable using an ordinary computer system rather than a specialized device. For example, it is possible to store and distribute, on a computer-readable recording medium (such as a CD-ROM or MO), a program for executing the foregoing operations on a computer connected to a network, whereby the moisture status measuring device 1 that executes the processes discussed earlier is constituted by installing the program onto a computer system.

Furthermore, the method of providing a program to a computer is arbitrary. For example, it is possible for a program to be uploaded to a bulletin board system (BBS) on a communication line, and delivered to a computer via the communication line. It is also possible for a program to be transmitted by a modulated wave obtained by modulating a carrier wave with a signal expressing a program, whereby a device receiving the modulated wave demodulates the modulated wave to restore the program. The computer then activates the program, and under control by an OS, executes the program similarly to other applications. Thus, the computer functions as the moisture status measuring device 1 that executes the processes discussed earlier.

Having described and illustrated the principles of this application by reference to one preferred embodiment, it should be apparent that the preferred embodiment may be modified in arrangement and detail without departing from the principles disclosed herein and that it is intended that the application be construed as including all such modifications and variations insofar as they come within the spirit and scope of the subject matter disclosed herein.

What is claimed is:

1. A moisture status measuring device comprising:
   a moisture amount sensor that acquires an output value according to an amount of moisture contained in soil;
   a drainage sensor that detects water discharge from the soil; and a moisture status deriver that derives moisture status information expressing a moisture status of the soil based on the output value acquired by the moisture amount sensor and the detection of the water discharge by the drainage sensor;

wherein the moisture status deriver derives the moisture status information according to the following formula:

$$\theta(t) = \frac{V(t) - V_o}{V_f - V_o} \times 100$$

where:

$\theta(t)$ is the moisture status information, $V(t)$ is a voltage value acquired by the moisture amount sensor as the output value at an arbitrary time t, $V_f$ is a voltage value acquired by the moisture amount sensor as the output value at a time when the drainage sensor detects the water discharge, and $V_o$ is a voltage value acquired by the moisture amount sensor as the output value in a state of dry soil.

2. The moisture status measuring device according to claim 1, further comprising:
a plant type-specific threshold value table that stores, for each type of plant, a type-specific threshold value at which each type of plant will grow;
a selector that selects a plant that will grow in the soil; and
a report controller that specifies the type-specific threshold value corresponding to a type of the plant selected by the selector from the plant type-specific threshold value table, and causes a reporter to report that watering of the soil should be performed or that watering of the soil is not allowed based on a moisture status value expressed by the moisture status information and the specified type-specific threshold value.

3. The moisture status measuring device according to claim 2, wherein the report controller controls the reporter to report that the moisture status of the soil is full when the drainage sensor detects the water discharge.

4. The moisture status measuring device according to claim 2, wherein the report controller controls the reporter to report that the watering of the soil is not allowed when the moisture status value expressed by the moisture status information is equal to or greater than the specified type-specific threshold value.

5. The moisture status measuring device according to claim 2, wherein the report controller controls the reporter to report that the watering of the soil should be performed when the moisture status value expressed by the moisture status information is less than the specified type-specific threshold value.

6. The moisture status measuring device according to claim 2, wherein the plant type-specific threshold value table stores the type-specific threshold value expressing an appropriate moisture status of the soil that grows the plant for each type of the plant.

7. The moisture status measuring device according to claim 2, further comprising:
a storage that stores the type-specific threshold value table;
wherein the report controller specifies the type-specific threshold value corresponding to the type of the plant selected by the selector from the plant type-specific threshold value table stored in the storage.

8. The moisture status measuring device according to claim 2, further comprising:

a transmitter that transmits the moisture status information derived by the moisture status deriver to outside;
wherein the report controller controls the transmitter to transmit the moisture status information to a communication terminal device.

9. The moisture status measuring device according to claim 8, wherein the report controller controls a communication terminal side reporter of the communication terminal device to report the moisture status information to a user.

10. The moisture status measuring device according to claim 9, wherein the communication terminal side reporter is a communication terminal side display that displays an image, a communication terminal side sound output device that outputs a sound, or a communication terminal side light emitter that emits light.

11. The moisture status measuring device according to claim 2, wherein the reporter is a display that displays an image, and
wherein the report controller reports the moisture status information to a user by controlling the display to display the moisture status information as the image.

12. The moisture status measuring device according to claim 2, wherein the reporter is a sound output device that outputs a sound, and
wherein the report controller reports the moisture status information to a user by controlling the sound output device to output the moisture status information as the sound.

13. The moisture status measuring device according to claim 2, wherein the reporter is a light emitter that emits light, and
wherein the report controller reports the moisture status information to a user by controlling an on/off, a luminous color, or an emission intensity of the light emitter, and emitting the light.

14. The moisture status measuring device according to claim 1, wherein the moisture amount sensor acquires the output value according to the amount of moisture contained in the soil housed in a container having a drain hole, and
wherein the drainage sensor detects water discharged from the drain hole.

15. The moisture status measuring device according to claim 14, wherein the moisture amount sensor has an electrode to be inserted into the soil, and detects a voltage value according to the moisture amount contained in the soil as the output value, and
wherein the drainage sensor is disposed on a pan that receives the water discharge discharged from the drain hole, and detects the water discharged from the soil to the pan.

16. The moisture status measuring device according to claim 1, wherein the moisture status information is indicated as a degree of moisture, taking 0 to be a state in which the soil is dry, and 100 to be a state of the soil at the time when the drainage sensor detects the water discharge.

17. A moisture status measurement method comprising:
acquiring an output value according to an amount of moisture contained in soil;
detecting water discharge from the soil; and
deriving moisture status information expressing a moisture status of the soil based on the acquired output value and the detection of the water discharge;
wherein the moisture status information is derived according to the following formula:

$$\theta(t) = \frac{V(t) - V_o}{V_f - V_o} \times 100$$

where:
θ(t) is the moisture status information,
V(t) is a voltage value acquired as the output value at an arbitrary time t,
$V_f$ is a voltage value acquired as the output value at a time when the water discharge is detected, and
$V_o$ is a voltage value acquired as the output value in a state of dry soil.

18. The moisture status measurement method according to claim 17, the moisture status measurement method using a plant type-specific threshold value table that stores, for each type of plant, a type-specific threshold value of the plant, and the moisture status measurement method further comprising:
   selecting a plant that will grow in the soil;
   specifying the type-specific threshold value corresponding to a type of the selected plant from the plant type-specific threshold value table, and performing control to report that watering of the soil should be performed or that watering of the soil is not allowed based on a moisture status value expressed by the moisture status information and the specified type-specific threshold value.

19. A non-transitory computer-readable medium storing a program, the program being executable by a computer of a moisture status measurement device including a moisture amount sensor and a drainage sensor, to control the moisture status measurement device to perform functions comprising:
   acquiring an output value according to an amount of moisture contained in soil, by the moisture amount sensor;
   detecting water discharge from the soil, by the drainage sensor; and
   deriving moisture status information expressing a moisture status of the soil based on the acquired output value and the detection of the water discharge;
   wherein the moisture status information is derived according to the following formula:

$$\theta(t) = \frac{V(t) - V_o}{V_f - V_o} \times 100$$

where:
θ(t) is the moisture status information,
V(t) is a voltage value acquired by the moisture amount sensor as the output value at an arbitrary time t,
$V_f$ is a voltage value acquired by the moisture amount sensor as the output value at a time when the drainage sensor detects the water discharge, and
$V_o$ is a voltage value acquired by the moisture amount sensor as the output value in a state of dry soil.

20. The non-transitory computer-readable medium according to claim 19, the moisture status measurement device using a plant type-specific threshold value table that stores, for each type of plant, a type-specific threshold value of the plant, and the functions further comprising:
   selecting a plant that will grow in the soil;
   specifying the type-specific threshold value corresponding to a type of the selected plant from the plant type-specific threshold value table, and performing control to report that watering of the soil should be performed or that watering of the soil is not allowed based on a moisture status value expressed by the moisture status information and the specified type-specific threshold value.

* * * * *